United States Patent [19]

Shieh et al.

[11] Patent Number: 5,646,330

[45] Date of Patent: Jul. 8, 1997

[54] PRODUCTION OF ENANTIOMERICALLY ENRICHED ORTHO-SUBSTITUTED α,α-DIAROMATIC METHANOLS

[75] Inventors: Wen-Chung Shieh, Berkeley Heights; William R. Cantrell, Summit; John Alan Carlson, Berkeley Heights, all of N.J.

[73] Assignee: Ciba-Geigy Corporation, Tarrytown, N.Y.

[21] Appl. No.: 390,255

[22] Filed: Feb. 17, 1995

[51] Int. Cl.$^6$ .................................................. C07C 229/34
[52] U.S. Cl. ............................ 560/43; 568/702; 568/707
[58] Field of Search ............................ 560/43; 568/702, 568/707

[56] References Cited

U.S. PATENT DOCUMENTS

| | | |
|---|---|---|
| 4,772,752 | 9/1988 | Brown . |
| 4,866,181 | 9/1989 | Brown ............................ 546/348 |
| 4,868,344 | 9/1989 | Brown . |
| 4,950,791 | 8/1990 | Brown . |
| 5,043,479 | 8/1991 | Brown . |
| 5,401,772 | 3/1995 | Yokoyama ........................... 514/539 |

OTHER PUBLICATIONS

Chemical & Pharmaceutical Bulletin, vol. 39, No. 10, 1991 Tokyo, Japan, pp. 2498-2501, M. Kato et al.
Guette et al, Tetrahedron 1979, 35, 1807-1815 "Effects Electroniques en Stereochimie-11".
Brown et al, Tetrahedron: Asymehetry 1992, 3, 841-844. "Preparative Synthesis of Optically Pure Ortho-Substituted Benzhydrols by Asymmetric Reductions of the Corresponding Benzophenones".
Wang et al, Synthesis 1989, 291-292 "Studies on Enantioselective Addition of Chiral Titanium Reagents to Aromatic Aldehydes".
Toda et al, Tetrahedron: Asymmetry 1991, 2, 873-874 "A New Preparative Method for Optically Active Diazylcarbinols".
King, J. Org. Chem. 1993, 58, 3731-3735 An Efficient Synthesis of LTD$_4$ Antagonist L-699,392.
Simpson et al, Synthetic Comm. 21, (15 & 16), 1705-1714, 1991. A Practical, One-Pot Preparation of Diisopinocampheylehloroborane.
Brown et al, J. Org. Chem. 1984, 49, 945-947 Improved Procedures for the Synthesis of Diisopinocampheylborane of High Optial Purity.
Brown, J. Org. Chem. 1989, 54, 1577 "Chiral Synthesis via Organoboranes. 22. Selective Reductions. 44. The Effect of the Steric Requirements of the Alkyl Substituent in Isopinocampheylalkylchloroboranes for the Asymmetric Reduction of Representative Ketones".

Ramachandran et al, Tetrahedron Letters 35, No. 14, 2141-2144, 1994. A Remarkable Inversion in Configuration of the Product Alcohols from the Asymmetric Reduction of ortho-Hydroxyacetophenones with B-Chlorodiisopinocampheylborane.
Nieminen et al; Tetrahedron Lett. 1987, 28, 4725-4728 "Selective Reduction of Ketones with Sodium Borohydride-Acetic Acid".
Brown et al, J. Am. Chem. Soc. 1988, 110, 1539-1546 "Chiral Synthesis via Organoboranes. 14. Selective Reductions. 41. Diisopinocampheylchloroborane, an Exceptionally Efficient Chiral Reducing Agent".
Brown et al, J. Org. Chem. 1992, 57, 2379 "Chiral Synthesis via Organoboranes. 34. Selective Reductions. 47. Asymmetric Reduction of Hindered αβ-Acetylenic Ketones".
Brown et al. Tetrahedron Asymmetry vol. 2 No. 5, pp. 339-342 (1991). "Asymmetric Reductions of Ketones using Lithium Aluminium Hydride Modified with N-N Dialkyl Derivatives of (R)-(-)-2-a Aminobutan-1-OL".

Primary Examiner—Joseph Conrad
Attorney, Agent, or Firm—Gregory D. Ferraro; Irving M. Fishman

[57] ABSTRACT

A method of producing compounds of formula I

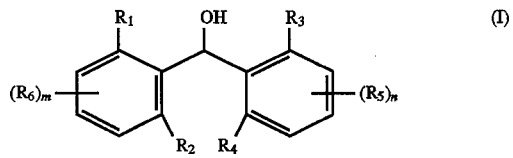

wherein one of $R_1$ and $R_2$ is selected from —OH, —SH, and —$NHR_7$; and the other of $R_1$ and $R_2$ is selected from H, —OH, —SH, —$NHR_7$, and $R_8$; $R_3$ and $R_4$ are each independently selected from $R_8$; n and m are each independently 3; and each $R_5$ and each $R_6$ is independently selected from —OH, —SH, —$NHR_7$, and $R_8$; and $R_8$ is as detailed in the specification;

in enantiomerically enriched form, comprising reducing a compound of formula II

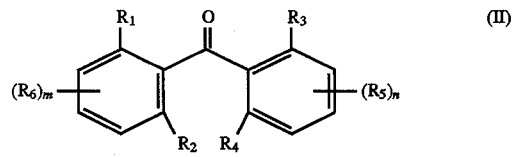

wherein $R_1$–$R_6$ are defined as in formula I, in the presence of B-haloisopinocampheylborane.

15 Claims, No Drawings

PRODUCTION OF ENANTIOMERICALLY ENRICHED ORTHO-SUBSTITUTED α,α-DIAROMATIC METHANOLS

FIELD OF THE INVENTION

The invention relates to the field of enantiomeric synthesis generally and to enantiomeric synthesis of asymetric α,α-diaromatic methanols, in particular.

BACKGROUND OF THE INVENTION

Asymmetric synthesis is becoming of greater and greater importance, particularly in the pharmaceutical industry. Increasingly, regulatory agencies are looking to have racemic active agents resolved into their respective enantiomers and only have the active enantiomer approved for marketing. Clearly, the mere ability to resolve a racemic mixture is important, but without a means to convert the non-active enantiomer to the active one, or a chiral synthesis, clearly 50% of the yield is lost at this point alone. Even where a resolution technique is available, it may frequently result in substantial losses in yield, or introduce an undesirable solvent into the manufacturing process. Hence, there is a continuing need for chiral synthetic pathways which yield the desired enantiomer in suitably high yields and purity thereby avoiding the significant losses of product and avoiding undesirable solvents that are otherwise associated with non-asymmetric synthetic techniques.

Recently, the asymmetric synthesis of benzhydrols has attracted considerable interest. Recent literature in this field has disclosed (1) asymmetric reduction of benzophenones with chiral Grignard reagents (Guette, et al., *Tetrahedron* 1979, 35, 1807–1815) or with lithium-aluminum hydride-chiral amino alcohol complexes (Brown et al, *Tetrahedron: Asymmetry* 1992, 3, 841–844 and Brown et al, *Tetrahedron:Asymmetry* 1991, 2, 339–342); (2) addition of chiral titanium reagents to aromatic aldehydes (Wang et al., *Synthesis* 1989, 291–292); and (3) resolution of benzhydrols by complexation with brucine (Toda et al., *Tetrahedron: Asymmetry* 1991, 2, 873–874).

OBJECTIVES

An objective of the present invention is to provide a convenient asymmetric synthetic process for the production of enantiomerically enriched α,α-diaromatic methanols.

Another object of the invention is to provide enantiomerically enriched α,α-diaromatic methanols in high yield and purity.

SUMMARY OF THE INVENTION

These and other objects of the present invention are achieved by a process which includes the reduction of an asymmetric biaromatic ketone of formula II

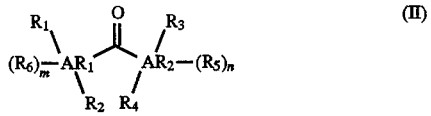

wherein $R_1$, $R_2$, $R_3$, and $R_4$ are all bound to atoms that are ortho to the central ketone between $AR_1$ and $AR_2$; $AR_1$ and $AR_2$ are each selected from aromatic carbocyclic and heterocyclic ring systems which are made up of one or two rings, of 5 to 7 members each and at least one of the rings in each bi-ring system is aromatic; one of $R_1$ and $R_2$ is selected from —OH, —SH, and —NHR$_7$; and the other of $R_1$ and $R_2$ is selected from H, —OH, —SH, —NHR$_7$, and $R_8$; $R_3$ and $R_4$ are each independently selected from H and $R_8$; n and m are each independently selected from 0 up to a number which is sufficient to fill the remaining available substituent positions of $AR_1$ and $AR_2$ respectively; and each $R_5$ and each $R_6$ is independently selected from H, —OH, —SH, —NHR$_7$, and $R_8$; and $R_8$ is as detailed below; in the presence of an isopinocampheylborane of formula III or IIIa

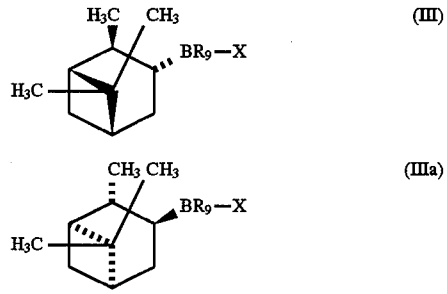

in which $R_9$ is $C_{1-6}$alkyl, $C_{5-6}$cycloalkyl, phenyl, or isopinocamphpheyl, and X is hydrogen or halogen, to yield a benzhydrol of formula I

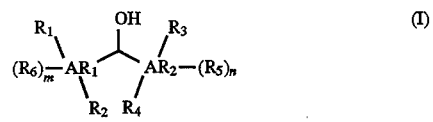

in enantiomerically enriched form.

DETAILED DESCRIPTION OF THE INVENTION

The present invention is the reduction of the keto bond of an prochiral ortho-substituted biaromatic ketone compound of formula II in the presence of an isopinocampheylborane of formula III or IIIa

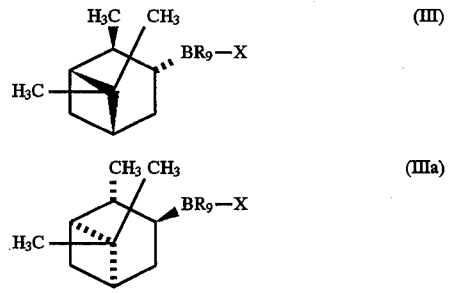

in which $R_9$ is $C_{1-6}$alkyl, $C_{5-6}$cycloalkyl, phenyl, or isopinocamphpheyl, and X is hydrogen or halogen, to yield the corresponding asymmetric biaromatic methanol of formula I in enantiomerically enriched form. In these compounds, X is preferably halogen, more preferably chlorine or bromine, most preferably chlorine. $R_9$ is preferably selected from methyl, ethyl, propyl, isopropyl, butyl, isobutyl, sec-butyl, tertiary butyl, thexyl (ie 2,1,1-trimethyl propyl), cyclopentyl, phenyl, or isopinocampheyl; more preferably isopinocampheyl. When $R_9$ is isopinocampheyl, it must be of the same configuration of the isopinocampheyl structure shown in formula III and IIIa respectively. Most preferably, the compound of formula III is (1R)-(–)-B-halodiisopinocampheylborane, and the compound of formula IIIa is (1S)-(+)-B-halodiisopinocampheylborane. Compounds of formulae III and IIIa may be used as such or may be prepared in situ, without isolation. Compounds of formulae III and IIIa are preferably prepared in the manner described in King, J. Org. Chem. 1993, 58, 3731–3735; Simpson, et al., Syn. comm. 21 (15 & 16), 1705–1714 (1991); Brown, J. Org. Chem. 1984, 49, 945; and/or Brown, J. Org. Chem 1989, 54 1577.

(1R)-(−)-B-chlorodiisopinocampheylborane, (1S)-(+)-B-chlorodiisopinocampheylborane, and their bromo counterparts are available through Aldrich Chemicals, as are isopinocampheol and isopinocampheylamine, chloroborane methyl sulfide, borane methyl sulfide, and α-pinene.

The compounds of formulae I and II are

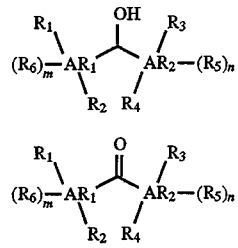

AR$_1$ and AR$_2$ are each independently selected from carbocyclic and heterocyclic ring systems having one or two fused rings each, with each ring having from 1 to 7 ring members, and at least the ring bound to R$_1$ and R$_3$ being aromatic. Preferably, at least one of AR$_1$ and AR$_2$ is carbocyclic, more preferably both are carbocyclic. When one or both of AR$_1$ and AR$_2$ are bicyclic, the ring of the bicyclic system which is attached to the ketone to be reduced is preferably carbocyclic, most preferably when both AR$_1$ and AR$_2$ are bicyclic, the ring of each bicyclic system which is attached to the ketone to be reduced is carbocyclic. In cases where both rings of the bicyclic ring system are aromatic, either ring may be attached to the ketone intended to be reduced. One particularly preferred group is when both AR$_1$ and AR$_2$ are the same ring system, whether mono or bi-cyclic, whether carbocyclic or heterocyclic. In all cases where either AR$_1$ or AR$_2$ are heterocyclic, the atom of the ring system which is bound to the carbonyl (between AR$_1$ and AR$_2$) intended to be reduced must be carbon.

More particularly, AR$_1$ and AR$_2$ carbocyclic rings are indepedendently selected from phenyl, naphthyl, indanyl, indenyl, tetrahydronaphthyl, dihydronaphthyl, cycloheptaphenyl, cycloheptadienphenyl, and cycloheptatrienphenyl, preferably phenyl and naphthyl, most preferably, phenyl. A highly preferred group of compounds of formula I and II are when both AR$_1$ and AR$_2$ are phenyl.

AR$_1$ and AR$_2$ heterocyclic mono ring systems include thienyl, furanyl, thiophenyl, pyridyl, pyrrolyl, imidazolyl, pyrazolyl, triazolyl, dithiolyl, oxathiolyl, oxazolyl, thiazolyl, oxadiazolyl, pyranyl, pyridazinyl, pytimidinyl, pyrazinyl, and triazinyl. In each of the forgoing rings, the heteroatoms can take any suitable position, such that the "term triazolyl" for example includes both 1,2,3-triazolyl as well as 1,2,4-triazolyl.

Preferred monocyclic heterorings for AR$_1$ and AR$_2$ include, furanyl, pyrrolyl, pyridyl, pyrazolyl, triazolyl, thiazolyl, pyranyl, pyridazinyl, pyrimidinyl, and triazinyl; more highly preferred are pyridyl, pyrazolyl, triazolyl, pyridazinyl, pyrimidinyl, and triazinyl; most highly preferred is pyridyl.

AR$_1$ and AR$_2$ heterocyclic bi-cyclic ring systems include those in which one or both rings are heteroaromatic, the other ring being carbocyclic or heterocyclic, and aromatic or not aromatic. In cases where both rings of the bicyclic ring system are aromatic, either ring may be attached to the ketone intended to be reduced. Such bicyclic aromatic ring systems include benzopyrrolyl, benzofuranyl, thionaphthenyl, benzoxazolyl, benzpyrazolyl, benzopyranyl, benzoxazinyl, quinolinyl, benzodiazinyl, pyrindenyl, pyranopyrrolyl, pyranopyranyl, pyanofuranyl, indolizinyl, naphthyridinyl, pyridopyridinyl, purinyl, pteridinyl, and their partial hydrogenated counterparts, provided that at least one heteroring of each fused ring system remains aromatic. In each of the above fused ring systems, the fused bond may be any side of either ring, and the heteroatoms may be in any suitable position, such that the term "benzodiazinyl" for example includes phthalazinyl, cinnolinyl, and quinazolinyl.

Preferred bicyclic rings are fused benzoheterorings, such as indolyl, benzofuranyl, benzopyranyl, quinolinyl, quinazolinyl, and the benzo(partially saturated)heteroring counterparts. Preferred bicyclic biherteroring systems include pyridopyridine, purine, and their partially saturated counterparts.

The reaction of the invention reduces the keto group shown in formula II

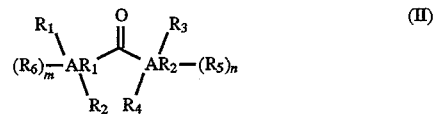

to the corresponding alcohol shown in formula I

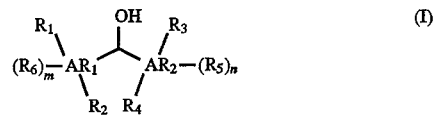

in substantial enantiomeric excess. In the compounds of formulae II and I, AR$_1$ and AR$_2$ are as defined above, R$_1$–R$_4$ are all ortho to the bond that connect the respective AR group to the central ketone (in formula II) or corresponding hydroxy group (in formula I). One of R$_1$ and R$_2$ must be selected from —OH, —SH, and —NHR$_7$; and the other of R$_1$ and R$_2$ is selected from H, —OH, —SH, —NHR$_7$, and R$_8$; preferably, one of R$_1$ and R$_2$ is —OH, and the other is selected from H, —OH, —SH, —NHR$_7$, and R$_8$; more preferably, the second of R$_1$ and R$_2$ is H or —OH. R$_7$ is selected from the group consisting of H, C$_1$–C$_7$alkyl, C$_1$–C$_7$alkanoyl, and C$_1$–C$_7$alkoxycarbonyl. Preferably, R$_7$ is selected from the group consisting of H, C$_1$–C$_7$alkyl, and C$_1$–C$_7$alkanoyl, more preferably, R$_7$ is H.

R$_3$ and R$_4$ are independently selected from the group consisting of H and R$_8$.

n and m are each independently an integer of from 0 to the number of free substitution positions on the AR group to which it relates. Preferably, n is 0 to 3, more preferably 0 or 1, most preferably one of m and n is 0 and the other of m and n is 1.

Each R$_5$ and each R$_6$ is independently selected from the group consisting of R$_8$, H, —OH, —SH, and —NHR$_7$ wherein R$_7$ is as defined above; preferably H and R$_8$.

R$_8$ is selected from formula IV below, halogen (preferably F, Cl, or Br, more preferably F), nitro, carboxy, —Si(R$_{14}$)$_3$ (in which each R$_{14}$ is independently selected from H, C$_1$–C$_3$alkyl, and phenyl), C$_1$–C$_7$alkoxy, C$_1$–C$_7$alkanoyloxy, C$_1$–C$_7$alkoxycarbonyl, C$_1$–C$_7$alkylthio, —N(R$_{15}$)$_2$ (in which each R$_{15}$ group is independently of the other R$_7$ or in which both R$_{15}$ groups together with the nitrogen to which they are attached form a ring of 5–6 ring members having 0–2 additional heteroatoms selected from N, O, or S), —C(O)—N(R$_{15}$)$_2$ (in which each R$_{15}$ group is independently of the other $R_7$ or in which both $R_{15}$ groups together with the nitrogen to which they are attached form a ring of 5–6 ring members having 0–2 additional heteroatoms selected from N, O, or S), unsubstitued or substituted phenoxy, unsubstituted or substitued phenylthio, the substituents on said phenyl groups in phenoxy and phenylthio being up to 3 and being independently selected from hydrogen, halogen, and trifluoromethyl. Preferably, $R_8$ is selected from formula IV below, carboxy, $C_1$–$C_7$alkoxy, and $C_1$–$C_7$alkanoyloxy. When two $R_{15}$ groups together with the nitrogen to which they are attached form a 5–6 membered ring, such ring is selected from pyrrolyl, pyrazolyl, triazolyl, oxazolyl, thiazolyl, oxadiazolyl, dioxazolyl, oxathiazolyl, pyridyl, diazinyl, triazinyl, oxazinyl, thiazinyl, oxathiazinyl, oxadiazinyl, and the partial and fully saturated counterparts thereof, each of which is unsubstituted or may be further substituted by $C_{1-7}$alkyl, or N-substituted (where appropriate) by $C_{1-7}$alkyl, carboxy, or $C_{1-7}$alkoxycarbonyl. Formula IV is

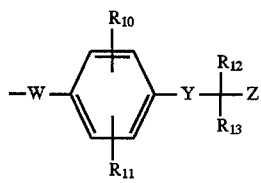

(IV)

in which W is O or S, preferably O; Y is O, S, or $NR_7$, preferably $NR_7$, more preferably, NH; $R_{10}$ and $R_{11}$ are each independently selected from H, halogen, $C_1$–$C_7$alkyl, and trifluoromethyl; $R_{12}$ is selected from hydrogen, $C_1$–$C_7$alkyl, and phenyl-$C_1$–$C_7$alkyl and $R_{13}$ is hydrogen; or $R_{12}$ and $R_{13}$ together are =O, preferably $R_{12}$ and $R_{13}$ together are =O; and Z is selected from —$COR_{16}$. $R_{16}$ is selected from OH, $C_1$–$C_7$alkoxy, (amino, acylamino, mono- or di-$C_{1-7}$alkylamino)-$C_1$–$C_7$alkoxy, carboxy-$C_1$–$C_7$alkoxy (e.g. alpha-carboxy-$C_1$–$C_7$alkoxy), $C_1$–$C_7$alkoxycarbonyl-$C_1$–$C_7$alkoxy (e.g. alpha-$C_1$–$C_7$alkoxycarbonyl-$C_1$–$C_7$alkoxy), α-(di-$C_{1-7}$alkylamino, albino, mono-$C_{1-7}$alkylamino, morpholino, piperidino, pyrrolidino, or 1-$C_{1-7}$alkylpiperazino)-carbonyl-$C_1$–$C_7$alkoxy, (carbocyclic or heterocyclic aryl, preferably phenyl or pyridyl)-$C_1$–$C_7$alkoxy (preferably methoxy) (which is unsubstituted or substituted in the aryl group with up to three substituents selected from halo, $C_{1-7}$alkyl, and $C_1$–$C_7$alkoxy), 1-(hydroxy, $C_1$–$C_7$alkanoyloxy, or $C_1$–$C_7$alkoxy)-$C_1$–$C_7$alkoxy (e.g. pivaloyloxymethoxy), (hydroxy, $C_1$–$C_7$alkanoyloxy, or $C_1$–$C_7$alkoxy)-$C_1$–$C_7$alkoxymethoxy, 1-($C_1$–$C_7$alkoxycarbonyloxy)-$C_1$–$C_7$alkoxy, phenoxy, substituted phenoxy (in which the phenyl ring has one to three substituents, each independently selected from the group consisting of $C_1$–$C_7$alkyl, halogen, and trifluoromethyl), 5-indanyloxy, 3-phthalidoxy, ($C_1$–$C_7$alkyl, $C_1$–$C_7$alkoxy or halo)-substituted-3-phthalidoxy, dihydroxypropyloxy, and —$N(R_{15})_2$ (in which each $R_{15}$ is as defined above), preferably OH, $C_1$–$C_7$alkoxy, and —$N(R_{15})_2$ with each $R_{15}$ preferably being independently selected from H and $C_1$–$C_7$alkyl. $R_{16}$ is preferably selected from OH, $C_1$–$C_7$alkoxy, phenoxy, substituted phenoxy (in which the phenyl ring has one to three substituents, each independently selected from the group consisting of $C_1$–$C_7$alkyl, halogen, and trifluoromethyl), and —$N(R_{15})_2$ (in which each $R_{15}$ is as defined above), preferably OH, $C_1$–$C_7$alkoxy, and —$N(R_{15})_2$ with each $R_{15}$ preferably being independently selected from H and $C_1$–$C_7$alkyl. Compounds in which $R_8$ is of formula IV are disclosed in U.S. Ser. No. 08/154,203, filed Nov. 18, 1993 and its corresponding European Application No. 938 10495.7.

In all of the foregoing groups within formula I–IV, subgroups that have carbon limits of $C_{1-7}$ are preferably $C_{1-4}$, more preferably are $C_{1-3}$. Each of these groups and subgroups may be either straight or branched.

Especially preferred ketone compounds for reduction in the present invention are those of formula II in which $AR_1$ is a phenyl ring, $AR_2$ is a phenyl ring, $R_1$ is hydroxy, $R_2$–$R_4$ are all hydrogen, n and m are each 1, $R_5$ is fluorine, and $R_6$ is of formula IV. Within this group, it is highly preferred that $R_5$ be para to and $R_6$ be meta to the ketone group between $AR_1$ and $AR_2$. Simultaneously, it is preferred that $R_6$ be para to $R_1$. Even more highly preferred within this group are those compounds in which formula IV is 4-(($C_{1-4}$alkoxycarbonyl or carboxy)-carbamoyl)-2,6-di($C_{1-4}$alkyl)-phenoxy.

The instant process comprises reducing a compound of formula II above with a borane compound of formula III or IIIa above to obtain a compound of formula I above in substantial enantiomeric excess. One of the enantiomers of the compounds having formula III or IIIa is either dissolved in a suitable solvent or prepared in situ for use in the invention process. Suitable solvents are selected from tetrahydrofuran, methylene chloride, ethyl ether, t-butyl methyl ether, toluene, and 1,2-dichloroethane, preferably tetrahydrofuran. After dissolving the compound of formula III or IIIa in the solvent, the temperature is reduced to from about −25° C. to about 25° C., preferably about −20° C. to about 20° C., more preferably about −17° C. to about 0° C., most preferably about −15° C. The ketone to be reduced (the compound of formula II) is added to this solution and held there for a period of from about 1 hour to about 72 hours, preferably about 2 hours to about 36 hours, more preferably about 2.5 hours to about 10 hours, most preferably about 3 hours. The reaction mixture is then warmed to from about −15° C. to about 35° C., preferably from about 0° C. to about 25° C., most preferably to about ambient temperature and subsequently treated with a tri$C_{1-4}$alkanolamine, preferably triethanolamine, and 3% hydrogen peroxide solution. Extractive isolation of the resultant solution with ethylacetate followed by column chromatography on silica gel, yields a high enantiomeric excess of one of the two enantiomers of the compound I (with respect to the chiral hydroxy group that results from the reduction. Use of the other enantiomer of the borane compound of formula III or IIIa yields the other enantiomer of the compound of formula I.

The compounds of formula III and IIIa, as stated can be utilized as pure compounds or can be made in situ, without isolation. As described by King et al, Simpson et al, and Brown et al, the particular enantiomer of formula III or IIIa can be obtained from the appropriate enantiomer of α-pinene in a number of ways. Reacting α-pinene with haloborane-methyl sulfide results in diisopinocampheylborane halide ($R_9$=isopinocampheyl and X=halogen). Reacting α-pinene with borane-methyl sulfide results in diisopinocampheylborane ($R_9$=isopinocampheyl and X=hydrogen), and if hydrohalic acid is present, the corresponding halide results. Hydroboration of α-pinene with $R_9BH(X)$ (with X=halogen) is also another method of making the compounds of formulae and IIIa.

Most compounds of formula II are readily available from commercial sources. As stated above, those wherein $R_8$ is of formula IV are described in U.S. Ser. No. 08/154,203, filed Nov. 18, 1993 and its corresponding European Application No. 938 10495.7, both of which are incorporated herein by reference.

The present invention will be more readily appreciated with reference to the following examples which are presented to illustrate, but not to limit, the claimed invention.

EXAMPLES

Example 1

(1R)-(−)-B-chlorodiisopinocampheylborane (0.321 g, 1 mmol/Aldrich) is dissoved in 2 ml of tetrahydrofuran (THF) and the solution is cooled to −20° C. A solution of the orthohydroxy benzophenone of formula A

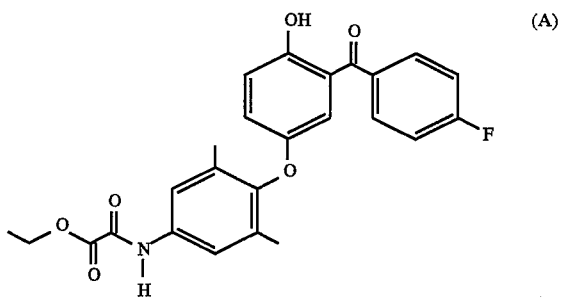

(0.226 g, 0.5 mmol) in 2 ml of THF is added and the mixture is stirred at −20° C. for a period of 3 hours. Triethanolamine (0.31 g, 2.1 mmol) in 1 ml of THF is added and the mixture is warmed to room temperature. Any precipitate is removed by filtration with the help of filter agent The filtrate is diluted with ethyl acetate and washed twice with water. The organic layer is analyzed by chiral HPLC using Diacel Chiralcel OJ 4.6 mm×250 mm, with the mobile phase being hexane/ethanol (80:20). The resultant product is found to be 98.3% of the (−)-enantiomer (not shown) and 1.7% of the (+)-enantiomer (shown below) of the benzhydrol of the formula B

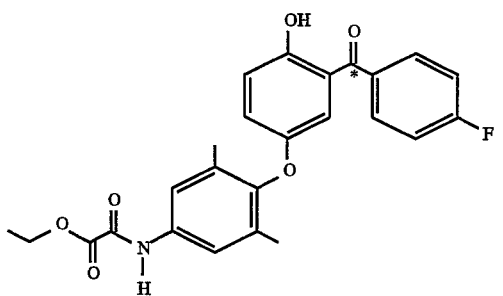

Example 2

0.301 g of (1 R)-(−)-B-chlorodiisopinocampheylborane (0.938 mmol) is cooled to −20° C. and a solution of 0.212 g (0.469 mmol) of compound A (as shown in Example 1) in 2 ml of THF is added via syringe. The mixture is stirred at −20° C. for 3 hours and 0.294 g (1.97 mmol) of triethanolamine in 1 ml THF is added, also at −20° C. The cooling bath is then removed and after 30 minutes 5 ml of ethyl acetate and 5 ml of sodium chloride are added. the organic layer is then filtered through a sep-pak silica cartridge (Waters Associates). Samples of unfiltered product having been subjected to HPLC analysis reveal that the product is 95.1 enantiomeric excess in favor of the (−)-enantiomer of the dibenzo alcohol, the (+)-enantiomer of which is shown in structure B in Example 1. Purification with silica gel column yields the (−)-enantiomer as a white solid. $[\alpha]^{25}_D = -21.0$ (c=1, acetonitrile)

Example 3

(1S)-(+)-B-chlorodiisopinocampheylborane (0.42 g, 1.31 mmol) and 2.5 ml of THF are added to a flask and then cooled to −20° C. A solution of 0.28 g (0.62 mmol) of compound A in 2.5 ml of THF are added via a syringe. The mixture is stirred at −20° C. for 4 hours. 0.39 g (2.62 mmol) of triethanolamine in 2.5 ml of THF is added and the cooling bath removed. The solution is allowed to come to room temperature with stirring (30 minutes). Filter agent (0.5 g/Aldrich) is added and the mixture filtered through a glass frit. the flask is rinsed with ethyl acetate which is used to wash the filtercake.

The filtrate is added to a separating funnel containing 10 ml of saturated sodium chloride. The organic layer is then filtered through a sep-pak silica cartridge (Waters). HPLC analysis indicates that the (+)-enantiomer shown as structure B in Example 1 is generated in 96.7% enantiomeric excess.

The crude reaction product (0.25 g) is purified by 25 g silica gel (230–400 mesh, 60 Angstrom/Aldrich) using a 2:3 ethyl acetate:hexane solvent system. Solvents are removed by rotovap to give a clear oil, which is dissolved in 0.5 ml ethyl acetate and 20 ml hexane is added, forming a white precipitate. Analysis of the product shows that the (+)-enantiomer shown in Example 1 as structure B is present in 95.5% enantiomeric excess. $[\alpha]^{25}_D = +21.5$ (c=1.1, acetonitrile)

Example 4

Ketone reduction with preparation of (1S)-(+)-B-chlorodiisopinocampheylborane in situ 13.2 mmol (2.1 ml) of 1S-(−)-α-pinene (97% optically pure/Aldrich) is charged into a 50 ml, 3 necked flask under nitrogen. 6 mmol (0.63 ml) of monochloroborane-methyl sulfide is added dropwise and the solution is stirred at 30°–35° C. for 2 hours. The resulting solution is then diluted with 10 ml of THF and cooled to −20° C.

A solution of 1.3 g (2.9 mmol) of the ortho-hydroxy benzophenone of formula A in 10 ml of THF is prepared and added to the above solution over a period of 1 hour. The mixture is stirred at −20° C. for a period of 2.5 hours. The mixture is then warmed to 0° C. and a solution of 30% hydrogen peroxide (1.5 g, 13 mmol), $K_2HPO_4 \cdot 3H_2O$ (1.69 g, 7.4 mmol), $KH_2PO_4$ (1 g, 7.4 mmol) in 13 ml of water is added. The mixture is stirred for an additional 15 minutes without cooling to give a precipitate. 20 ml of ethyl acetate is added to the mixture and the organic phase is separated, washed with 10% sodium bisulfite (1.35 g, 13 mmol, in 12 ml of water) at 15° C. The organic layer is separated and washed with 15 ml of saturated sodium chloride. Solvent is then evaporated and the product purified with a silica gel column (90 g, 200–400 mesh) eluting with hexane/ethyl acetate (1:1) to yield 0.81 g, 61.7%, of white solid 96.0% of which is the (+)-enantiomer of the benzhydrol of the formula B and 3.9% of which is the (−)-enantiomer.

Example 5

2.1 g (6.6 mmol) of (1R)-(−)-B-chlorodiisopincampheylborane is dissolved in 12 ml of THF and cooled to −20° C. A solution of 0.595 g (3 mmol) of o-hydroxybenzophenone in 10 ml of THF is added over 1 hour and stirred for another 3 hours at −15° C. to −20° C. Thereafter the mixture is warmed to 0° C. A solution of 2.1 g (13.9 mmol) of triethanolamine in 5ml of THF is added and the mixture is stirred at room temperature for 1.5 hours to yield a white precipitate.

The precipitate is removed by filtration and a solution of 30% hydrogen peroxide (0.75 g, 6.5 mmol), $K_2HPO_4 \cdot 3H_2O$ (0.85 g, 3.7 mmol), $KH_2PO_4$ (0.5 g, 3.7 mmol) in 6.5 ml water is added at 0° C. The mixture is stirred for another 15 minutes. Water (50 ml) and ethylacetate (30 ml) are added and the organic layer separated. A solution of 10% NaHSO₃ (0.7 g) in 12 ml of water is then added at 0° C. and the organic layer separated, washed with 12 ml of water and saturated sodium chloride, and dried over magnesium sulfate. solvent is then evaporated by vacuum to obtain 2.2 g of an oil. Product is further purified with silica gel column (60 g, 200–400 mesh) eluting with hexane:ethylacetate (4:1) to obtain 1.1 g of oil. Trituration with hexane yields crystals in 96.4% enantiomeric excess for use as seeds in further crystallizations. Seeding yields 99% pure enantiomer of the structure. $[\alpha]^{25}_D = -10.0$ (c=1.04, acetonitrile)

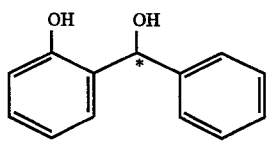

Example 6

One gram (3.12 mmol) of (1R)-(−)-B-diisopinocampheyl chloride is dissolved into 2 ml of THF and cooled to −20° C. To this is added a solution of 0.3 g (1.5 mmol) of o-amino-benzophenone in 2 ml of THF. the mixture is stirred for 3 hours at −15° to −20° C. and then warmed to 25° C. The mixture is then stirred at room temperature for an additional 72 hours. A solution of 0.736 (7 mmol) of diethanolamine in 2 ml of THF is added and stirred for 1 hour. The precipitate is filtered and the filtrate is diluted with 5 ml of ethylacetate. The organic layer is stirred with a solution of 0.8 g of 30% hydrogen peroxide, 0.8 g K₂PO₄·3H₂O, and 0.5 g KH₂PO₄ in 3.75 ml of water for 30 minutes. The organic layer is separated and washed with 10% NaHSO₃ (once, 6 ml), water (once, 6 ml), and saturated NaCl (once, 6 ml). Solvent is evaporated to dryness and the crude product is analyzed with chiral HPLC. A yield of 70.3% is obtained with 94% being the desired enantiomer shown below and 6% being the undesired enantiomer for an enantiomeric excess of 88%.

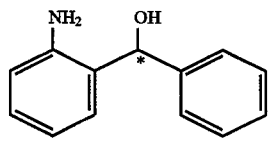

We claim:

1. A process for the production of an enantiomer of a compound of formula I

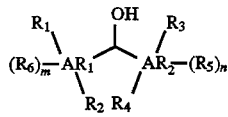

in a substantial enantiomeric excess comprising reducing a compound of formula II

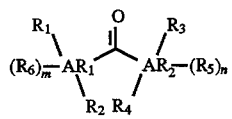

with a reducing agent selected from those compounds of formula III or IIIa

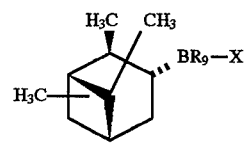

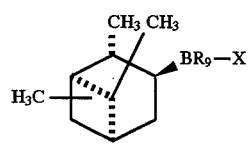

wherein

AR₁ and AR₂ are each independently selected from carbocyclic and heterocyclic ring systems having one or two fused rings each, with each ring having from 1 to 7 ring members, and at least the ring bound to R₁ and R₃ being aromatic;

n and m are each independently an integer of from 0 to the number of free substitution positions on the AR group to which it relates;

R₁–R₄ are all ortho to the bond that connect the respective AR group to the central ketone (in formula II) or corresponding hydroxy group (in formula I);

one of R₁ and R₂ must be selected from —OH, —SH, and —NHR₇; and the other of R₁ and R₂ is selected from H, —OH, —SH, —NHR₇, and R₈;

R₃ and R₄ are independently selected from the group consisting of H and R₈;

each R₅ and each R₆ is independently selected from the group consisting of R₈, H, —OH, —SH, and —NHR₇;

R₇ is selected from the group consisting of H, C₁-C₇alkyl, C₁-C₇alkanoyl, and C₁-C₇alkoxycarbonyl;

R₈ is selected from formula IV below, halogen, nitro, carboxy, —Si(R₁₄)₃ (in which each R₁₄ is independently selected from H, C₁-C₃alkyl, and phenyl), C₁-C₇alkoxy, C₁-C₇alkanoyloxy, C₁-C₇alkoxycarbonyl, C₁-C₇alkylthio, —N(R₁₅)₂ (in which each R₁₅ group is independently of the other R₇ or in which both R₁₅ groups together with the nitrogen to which they are attached form a ring of 5–6 ring members having 0–2 additional heteroatoms selected from N, O, or S), —C(O)—N(R₁₅)₂ (in which each R₁₅ group is independently of the other R₇ or in which both R₁₅ groups together with the nitrogen to which they are attached form a ring of 5–6 ring members having 0–2 additional heteroatoms selected from N, O, or S), unsubstitued or substituted phenoxy, unsubstituted or substitued phenylthio, the substituents on said phenyl groups in phenoxy and phenylthio being up to 3 and being independently selected from hydrogen, halogen, and trifluoromethyl;

formula IV is

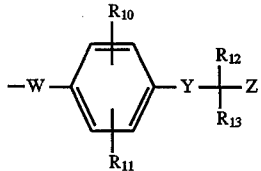

in which W is O or S;

Y is O, S, or NR₇;

R₁₀ and R₁₁ are each independently selected from H, halogen, C₁-C₇alkyl, and trifluoromethyl;

$R_{12}$ is selected from hydrogen, $C_1$–$C_7$alkyl, and phenyl-$C_1$–$C_7$alkyl; and $R_{13}$ is hydrogen; or $R_{12}$ and $R_{13}$ together are =O; and Z is selected from —$COR_{16}$; in which $R_{16}$ is selected from OH, $C_1$–$C_7$alkoxy, (amino, acylamino, mono- or di-$C_{1-7}$alkylamino)-$C_1$–$C_7$alkoxy, carboxy-$C_1$–$C_7$alkoxy, $C_1$–$C_7$alkoxycarbonyl-$C_1$–$C_7$alkoxy, α-(di-$C_{1-7}$alkylamino, amino, mono-$C_{1-7}$alkylamino, morpholino, piperidino, pyrrolidino, or 1-$C_{1-7}$alkylpiperazino)-carbonyl-$C_1$–$C_7$alkoxy, (carbocyclic or heterocyclic aryl)-$C_1$–$C_7$alkoxy (which is unsubstituted or substituted in the aryl group with up to three substituents selected from halo, $C_{1-7}$alkyl, and $C_1$–$C_7$alkoxy), 1-(hydroxy, $C_1$–$C_7$alkanoyloxy, or $C_1$–$C_7$alkoxy)-$C_1$–$C_7$alkoxy, (hydroxy, $C_1$–$C_7$alkanoyloxy, or $C_1$–$C_7$alkoxy)-$C_1$–$C_7$alkoxymethoxy, 1-($C_1$–$C_7$alkoxycarbonyloxy)-$C_1$–$C_7$alkoxy, phenoxy, substituted phenoxy (in which the phenyl ring has one to three substituents, each independently selected from the group consisting of $C_1$–$C_7$alkyl, halogen, and trifluoromethyl), 5-indanyloxy, 3-phthalidoxy, ($C_1$–$C_7$alkyl, $C_1$–$C_7$alkoxy or halo)-substituted-3-phthalidoxy, dihydroxypropyloxy, and —$N(R_{15})_2$ (in which each $R_{15}$ is as defined above), $R_9$ is $C_{1-6}$alkyl, $C_{5-6}$cycloalkyl, phenyl, or isopinocampheyl (of the same configuration as the other isopinocampheyl group in the molecule); and X is hydrogen or halogen.

2. The process of claim 1 wherein the compound of formula III or IIIa is either (1S)-(+)-B-diisopinocampheylborane chloride or (1R)-(−)-B-diisopinocampheylborane chloride.

3. The process of claim 1 wherein each of $AR_1$ and $AR_2$ are independently selected from phenyl, naphthyl, pyridyl, pyrimidinyl, and triazinyl.

4. The process of claim 1 wherein each of $AR_1$ and $AR_2$ are the same ring system but are independently unsubstituted or substituted provided that the number, kind, and position of substituents on $AR_1$ are not identical to the number, kind, and position of substituents on $AR_2$.

5. The process of claim 1 wherein $AR_1$ and $AR_2$ are each phenyl rings which are unsubstimted or substituted as indicated in claim 1.

6. The process of claim 1 wherein at least one of $R_1$ and $R_2$ is selected from —OH, and —$NHR_7$.

7. The process of claim 1 wherein at least one of $R_1$ and $R_2$ is selected from —OH.

8. The process of claim 1 wherein n and m are each independently selected from 0 to 3.

9. The process of claim 1 wherein each of $R_5$ and $R_6$ is independently selected from the group consisting of H and $R_8$.

10. The process of claim 1 wherein each $R_7$ is independently selected from the group consisting of H, $C_1$–$C_7$alkyl, and $C_1$–$C_7$alkanoyl.

11. The process of claim 1 wherein each $R_7$ is H.

12. The process of claim 1 wherein each $R_8$ is independently selected from groups of formula IV.

13. The process of claim 1 wherein $R_{12}$ and $R_{13}$ together are oxo.

14. The process of claim 13 wherein $R_{16}$ is selected from OH, $C_1$–$C_7$alkoxy, phenoxy, substituted phenoxy (in which the phenyl ring has one to three substituents, each independently selected from the group consisting of $C_1$–$C_7$alkyl, halogen, and trifluoromethyl), and —$N(R_{15})_2$ with each $R_{15}$ being independently selected from H and $C_1$–$C_7$alkyl.

15. The process of claim 1 further comprising forming the compound of formula III or the compound of formula IIIa in situ prior to the addition of the compound of formula II which comprises (a) reacting the appropriate enantiomer of α-pinene with a haloborane-methyl sulfide or borane-methyl sulfide or (b) reacting the appropriate enanfiomer of α-pinene with boran-methyl sulfide in the presence of a hydrohalic acid, or (c) hydroborating α-pinene with $R_9BH$ (X).

* * * * *

UNITED STATES PATENT AND TRADEMARK OFFICE
CERTIFICATE OF CORRECTION

PATENT NO. : 5,646,330
DATED : July 8, 1997
INVENTOR(S) : Wen-Chung Shieh, William R. Cantrell, and John Alan Carlson It is certified that error appears in the above-identified patent and that said Letters Patent is hereby corrected as shown below:

Column 7, formula B, lines 33 to 45, that portion of the formula reading:

Signed and Sealed this

Seventeenth Day of February, 1998

Attest:

BRUCE LEHMAN

Attesting Officer                Commissioner of Patents and Trademarks